United States Patent
Xu et al.

(10) Patent No.: US 11,210,779 B2
(45) Date of Patent: Dec. 28, 2021

(54) DETECTION AND QUANTIFICATION FOR TRAUMATIC BLEEDING USING DUAL ENERGY COMPUTED TOMOGRAPHY

(71) Applicant: Siemens Healthcare GmbH, Erlangen (DE)

(72) Inventors: Zhoubing Xu, Plainsboro, NJ (US);
Sasa Grbic, Plainsboro, NJ (US);
Shaohua Kevin Zhou, Plainsboro, NJ (US); Philipp Hölzer, Baltimore, MD (US); Grzegorz Soza, Heroldsberg (DE)

(73) Assignee: Siemens Healthcare GmbH, Erlangen (DE)

( * ) Notice: Subject to any disclaimer, the term of this patent is extended or adjusted under 35 U.S.C. 154(b) by 146 days.

(21) Appl. No.: 16/124,460

(22) Filed: Sep. 7, 2018

(65) Prior Publication Data
US 2020/0082525 A1    Mar. 12, 2020

(51) Int. Cl.
*G06K 9/00* (2006.01)
*G06T 7/00* (2017.01)

(52) U.S. Cl.
CPC .. *G06T 7/0012* (2013.01); *G06T 2207/10081* (2013.01); *G06T 2207/20081* (2013.01); *G06T 2207/20084* (2013.01); *G06T 2207/30104* (2013.01)

(58) Field of Classification Search
CPC ......... G06T 7/0012; G06T 2207/10081; G06T 2207/20081; G06T 2207/30104; G06T 2207/20084; G06T 2207/30101; A61B 6/5217; A61B 5/02042; A61B 6/4014; A61B 6/482; A61B 6/032; A61B 6/03; A61B 6/504; A61B 6/52
USPC ........................................................ 382/131
See application file for complete search history.

(56) References Cited

U.S. PATENT DOCUMENTS

| | | | |
|---|---|---|---|
| 2011/0060247 A1* | 3/2011 | Payne | A61B 6/505 600/587 |
| 2011/0280458 A1* | 11/2011 | Flohr | G06T 5/002 382/131 |
| 2012/0076377 A1* | 3/2012 | Dutta | A61B 6/032 382/131 |
| 2018/0168490 A1* | 6/2018 | Jones | A61B 5/742 |
| 2018/0218794 A1* | 8/2018 | Hoelzer | G16H 50/50 |
| 2018/0365824 A1* | 12/2018 | Yuh | G06T 7/0012 |
| 2019/0021677 A1* | 1/2019 | Grbic | A61B 5/7292 |

(Continued)

OTHER PUBLICATIONS

Yu L, Christner JA, Leng S, Wang J, Fletcher JG, McCollough CH. Virtual monochromatic imaging in dual-source dual-energy CT: radiation dose and image quality. Med Phys. 2011 ;38(12):6371-6379. doi: 10.1118/1.3658568 (Year: 2011) (Year: 2011).*

(Continued)

*Primary Examiner* — Van D Huynh

(57) ABSTRACT

Systems and methods are provided for automatic detection and quantification for traumatic bleeding. Image data is acquired using a full body dual energy CT scanner. A machine-learned network detects one or more bleeding areas on a bleeding map from the dual energy CT scan image data. A visualization is generated from the bleeding map. The predicted bleeding areas are quantified, and a risk value is generated. The visualization and risk value are presented to an operator.

14 Claims, 6 Drawing Sheets

(56) References Cited

U.S. PATENT DOCUMENTS

2019/0325621 A1* 10/2019 Wang .................... A61B 6/037
2020/0297219 A1*  9/2020 Mitra .................. G06N 3/0472

OTHER PUBLICATIONS

Yu L, Christner JA, Leng S, Wang J, Fletcher JG, McCollough CH. Virtual monochromatic imaging in dual-source dual-energy CT: radiation dose and image quality. Med Phys. 2011;38(12):6371-6379. doi: 10.1118/1.3658568 (Year: 2011).*

Kim, S. J., et al. "Dual-energy CT in the evaluation of intracerebral hemorrhage of unknown origin: differentiation between tumor bleeding and pure hemorrhage." American Journal of Neuroradiology 33, No. 5 (2012): 865-872.

* cited by examiner

DETECTION AND QUANTIFICATION FOR TRAUMATIC BLEEDING USING DUAL ENERGY COMPUTED TOMOGRAPHY

FIELD

The present embodiments relate to medical computed tomography imaging and diagnosis.

BACKGROUND

Traumatic bleeding is one of the leading causes for death upon accidents. Traumatic bleeding requires immediate treatment and emergent care. More than 50% of all trauma patients with a fatal outcome die within 24 hours of injury. Appropriate management of a trauma patient with massive bleeding includes the early identification of potential bleeding sources followed by prompt measures to minimize blood loss, restore tissue perfusion and achieve stability. However, detection of the traumatic bleeding is very challenging, especially when there are no apparent defects on the surfaces of skin or skull.

Computed Tomography (CT) has been used previously for scanning of trauma patients. Using CT scanners, total whole-body scanning time may be reduced to less than 30 seconds. While CT scanners are able to capture images of a trauma patient, the analysis of the resulting data is difficult and unwieldy, particularly to identify bleeding. Potential bleeding may be located everywhere (e.g., brain, GI, chest, abdomen, etc.) on a patient, so bleeding is to be distinguished from a large variety of surrounding structures. Further, there is a huge variability of appearances of bleeding. In addition, for CT images, bleeding areas may be depicted with similar intensity values with other structures, for example bones and vessels, that may complicate diagnosing areas.

SUMMARY

By way of introduction, the preferred embodiments described below include embodiments for automatic detection and quantification for traumatic bleeding. Image data is acquired using a full body dual energy CT scan. A machine-learned network generates a bleeding probability map from the dual energy CT scan. A visualization is generated from the bleeding probability map. The predicted bleeding areas are quantified, and a risk value is generated. The visualization and risk value are presented to an operator.

In a first aspect, a method is provided for detecting bleeding areas in a patient. Dual energy image data is acquired using a dual energy CT full body scan of the patient. Bleeding areas are detected on a bleeding area map using a neural network trained to identify and classify one or more bleeding areas given dual energy image data. A visualization of the bleeding map is generated and displayed.

In a second aspect, a method is provided for automatically assessing traumatic bleeding. DECT image data of a patient is acquired using a dual energy CT scan. Bone material is removed from the DECT image data. Vessels are traced in the DECT image data. One or more bleeding areas are predicted using a first machine-learned network trained to identify and classify bleeding areas given DECT image data. A severity rating for the one or more bleeding areas is determined. A size for the one or more bleeding areas is calculated. A grade is generated for the one of more bleeding areas as a function of the size and severity ratings of the one or more bleeding areas. A risk value for the patient is estimated using a second machine-learned network trained to formulate an overall risk.

In a third aspect, a system is provided for automatically assessing traumatic bleeding. The system includes a dual energy computer tomography scanner, an image processor, and a display. The dual energy computer tomography scanner is configured to acquire high KV CT image data and low KV CT image data of a patient. The image processor is configured to input the high KV CT image data and low KV CT image data into a machine-learned network trained to predict bleeding areas given image data; the image processor further configured to generate a visualization of bleeding areas predicted by the machine-learned network. The display is configured to display the visualization.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION

Embodiments provide for detecting and quantifying traumatic bleeding using a full body scan. A dual energy CT scan is performed on a patient to generate multiple imaging datasets. The multiple imaging datasets are input into a machine-learned network that is trained to identify areas with bleeding based on the different imaging datasets. The areas are automatically quantified and graded. An overall risk assessment is provided to an operator.

Figure 1:
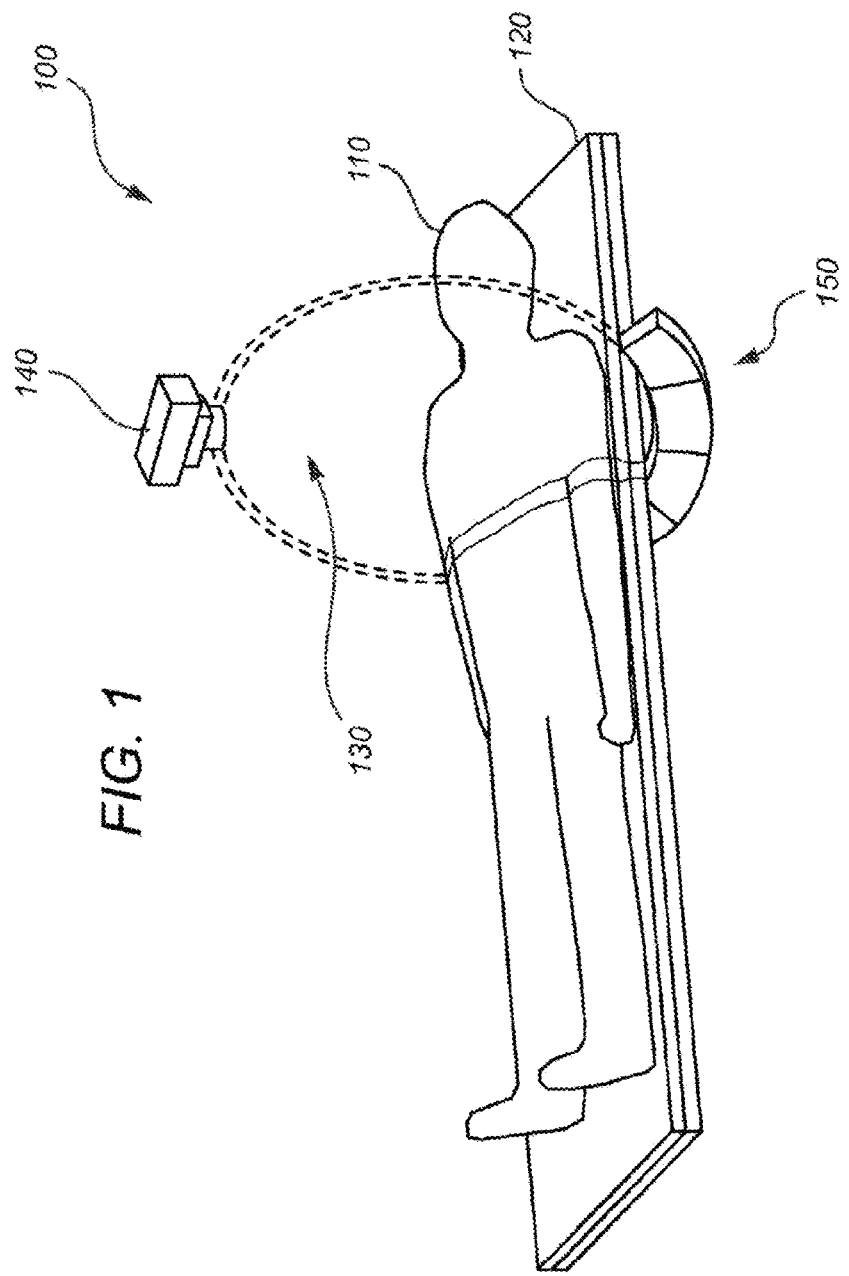
FIG. 1 depicts an example of a CT system.

FIG. 1 depicts an example CT imaging system 100. An object 110 (e.g., a patient) is positioned on a table 120 that is configured, via a motorized system, to move the table to multiple positions through a circular opening 130 in the CT imaging system 100. An X-ray source 140 (or other radiation source) and detector element(s) 150 are a part of the CT imaging system and are configured to rotate around the subject 110 on a gantry while the subject is inside the opening 130. The rotation may be combined with movement of the bed to scan along a longitudinal extent of the patient. Alternatively, the gantry moves the source 140 and detector 150 in a helical path about the patient. In a CT imaging system 100, a single rotation may take approximately one second or less. During the rotation of the X-ray source 140 and/or detector, the X-ray source 140 produces a narrow, fan-shaped (or cone-shaped) beam of X-rays that pass through a targeted section of the body of the subject 110 being imaged. The detector element(s) 150 (e.g., multi-ring detector elements) are opposite the X-ray source 140 and register the X-rays that pass through the body of the subject being imaged and, in that process, record a snapshot used to create an image. Many different snapshots at many angles through the subject are collected through one or more rotations of the X-ray source 140 and/or detector element(s) 150. The image data generated by the collected snapshots are transmitted to a control unit that stores or processes the image data based on the snapshots into one or several cross-sectional images or volumes of an interior of the body (e.g., internal organs or tissues) of the subject being scanned by the CT imaging system 100.

While a CT scan is useful for certain medical diagnosis, for detecting traumatic bleeding a standard CT scan includes drawbacks. For identification and quantification, a generic solution for the whole body is required as the potential locations of bleeding may be anywhere (e.g., brain, GI, chest, abdomen, etc.). Additionally, there is a huge variability of appearances of traumatic bleeding over different regions and different types of injuries. Finally, bleeding areas may include similar intensity values with other structures, e.g. bones and vessels.

Figure 2:
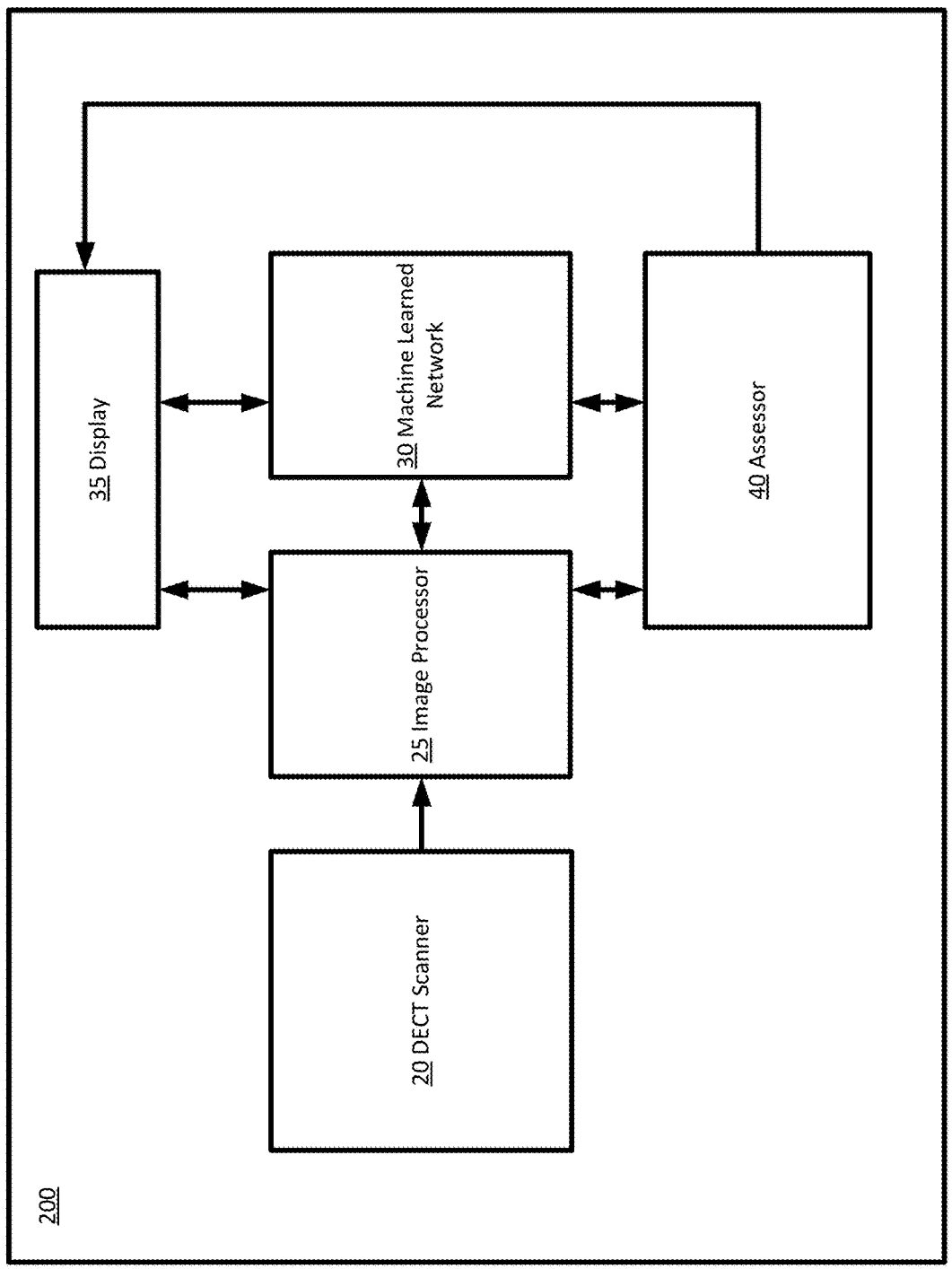
FIG. 2 depicts a system for automated detection and quantification for traumatic bleeding according to an embodiment.

Embodiments provide for detecting and quantifying traumatic bleeding using a dual energy CT (DECT) scan. FIG. 2 depicts an example system 200 for detecting and quantifying traumatic bleeding. The system 200 of FIG. 2 includes a DECT scanner 20, an image processor 25, a machine-learned network 30, a display 35, and an assessor 40. The image processor 25, machine-learned network 30, and assessor 40 may be components or modules in a computer, server, or cloud computing environment. Additional, different, or fewer components may be provided, such as not including the display 35 where the output is stored in a memory or transferred over a network.

The DECT scanner 20 acquires images at two different energy levels (kV levels). The image processor 25 uses a material map to segment and process the image, for example, to identify different materials based on their intensities at the two CT images. The material map and the differences in the two CT images helps differentiate materials with similar intensity value as opposed to the single energy CT images. The machine-learned network 30 is configured to automatically identify a bleeding area given image data from the image processor 25. The machine-learned network takes the two levels of CT images as inputs and generates the traumatic bleeding probability map as output. The bleeding area(s) are quantified by the assessor 40 based on clinical reports. The display 35 is configured to display the assessment and a visualization generated by the image processor 25 the machine-learned network. The output of the efficient process is an accurate assessment of traumatic bleeding in a patient.

Figure 3:
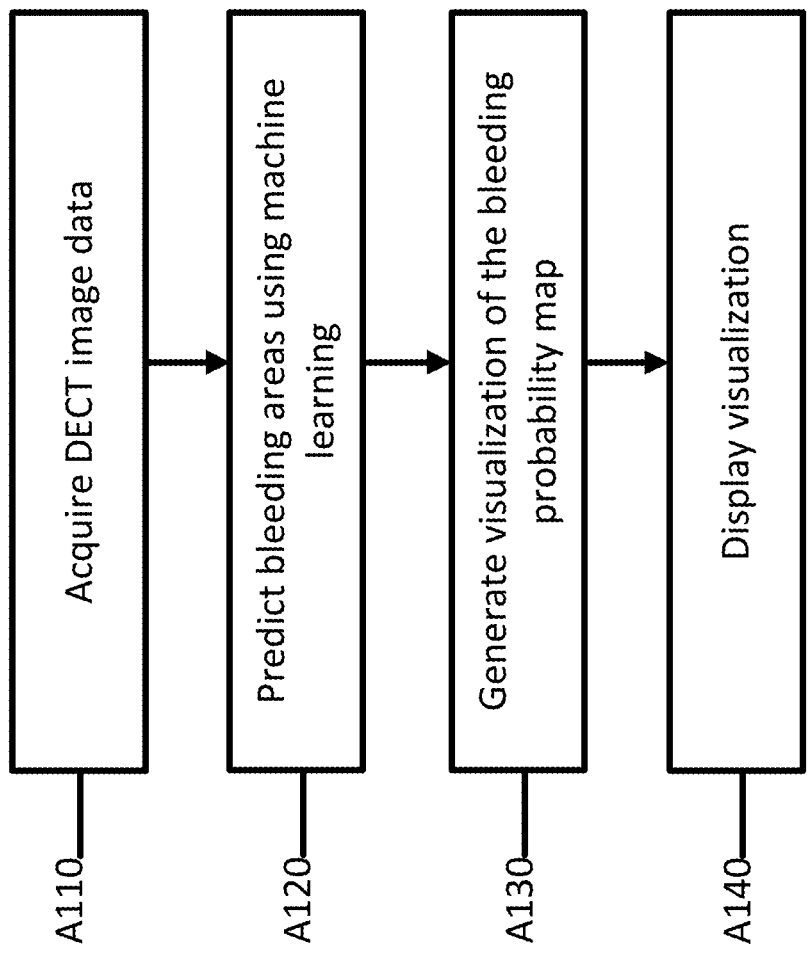
FIG. 3 depicts a method for automated detection of traumatic bleeding according to an embodiment.

FIG. 3 depicts one embodiment of a method for detecting traumatic bleeding. The acts are performed by the system of FIG. 2, FIG. 4, FIG. 6, other systems, a workstation, a computer, and/or a server. The acts are performed in the order shown (e.g., top to bottom) or other orders. Additional acts may be performed such as processing DECT image data from the scan prior to input into a machine-learned network 30.

At act A110, DECT image data (also referred to as dual energy image data) of an object is acquired using a DECT scanner. The DECT image data may be scalar values (e.g.,  attenuation coefficients or Hounsfield units) or may be imaging data (e.g. medical imaging data) to be used to form an image. The data, images, or imaging data is made available by or within the medical imaging device. Alternatively, the acquisition is from storage or memory, such as acquiring a previously created dataset from a picture archiving and communication system (PACS). A processor may extract the data from a picture archive communications system or a medical records database. The DECT image data includes two or more datasets that are acquired by the scan of the object (e.g. patient) using two different energy levels. Additional datasets may be acquired or derived from the acquired data.

The DECT image data is data representing a two-dimensional slice or a three-dimensional volume of the patient. For example, each dataset of the DECT image data represents an area or slice of the patient as pixel values. As another example, the DECT image data represents a volume or three-dimensional distribution of voxels. The three-dimensional representation may be formatted as a stack or plurality of two-dimensional planes or slices or as voxels in a grid. Values are provided for each of multiple locations distributed in two or three dimensions.

The data may be in any format. While the terms image and imaging are used, the image or imaging data may be in a format prior to actual display of the image. For example, the imaging data may be a plurality of scalar values representing different locations in a Cartesian or polar coordinate format different than a display format. As another example, the image may be a plurality red, green, blue (e.g., RGB) values output to a display 35 for generating the image in the display format. The imaging data is a dataset that may be used for imaging, such as scan data or a generated image representing the patient. For a three-dimensional image, the raw data from the detector may be reconstructed into a three-dimensional representation. The imaging data represents tissue, fluid, and/or bone of the patient.

The DECT image data is acquired using a DECT scan. During the DECT scan, two or more sets of data may be acquired using two or more different energy levels. Conventional single energy CT (SECT) uses a single polychromatic X-ray beam (ranging from 70 to 140 kVp, for example typically 120 kVp) emitted from a single source and received by a single detector. The contrast of a SECT image dataset depends on differences in photon attenuation of the various materials that constitute the object (e.g. soft tissue, air, calcium, fat, of a human body). The degree that a material will attenuate the X-ray beam is dependent on the tissue composition and the photon energy level and how closely it exceeds a k-edge (e.g. the inner electron shell binding energy) of the material.

Although similar to a SECT scan, the DECT scan uses two (or more) energy levels (for example, 80 and 140 kVp) to acquire data that is processed to generate the two of more datasets (e.g. one for each energy level). The multiple datasets provide for analysis of material composition through image acquisition at two different energy levels. Materials, e.g. tissues, fluids, etc. have unique attenuation profiles at different energy levels according to a linear attenuation coefficient. The multiple datasets provide a view of tissues when exposed to both low and high-energy X-ray beams. Materials with low atomic numbers (e.g. water) demonstrate small differences in attenuation between high and low X-ray energies while materials with high atomic numbers (e.g. iodine) show large differences in attenuation at different photon energies. The two energy levels may be adjusted depending on the scanner used, the patient, and/or a material map that is used.

Different scanners may be used to perform the DECT scan. For example, a dual source DECT (dsDECT) scanner utilizes two X-ray tubes and two detectors to obtain simultaneous dual energy acquisition and data processing. A single source DECT (ssDECT) scanner uses a single X-ray tube that rapidly alternates between low and high energies (fast-switching) and a single detector that quickly registers information from both energies. For a detector based spectral CT, a single X-ray tube with full dose modulation capabilities is paired with a detector made of two layers (sandwich detector) that simultaneously detects two energy levels. Alternative scanners or DECT techniques may be used to acquire the DECT image data. Different hospitals or organizations may use different protocols or different scanners. The methods described herein may be tailored to a specific scanner, specific organization, or may be used globally across all scanner types and parameters. In an embodiment, multi energy CT (MECT) may be sued. MECT uses photon counting detectors to identify materials in an image. In MECT, multiple energy-selective measurements of the attenuation of the patient are obtained. MECT may be used to create mono-energetic images for use in detecting bleeding areas. MECT data is used to with one or more algorithms to generate a set of material-specific parameters, such as effective atomic number and density. The material-specific parameters may be used to identify materials and bleeding areas.

Figure 4:
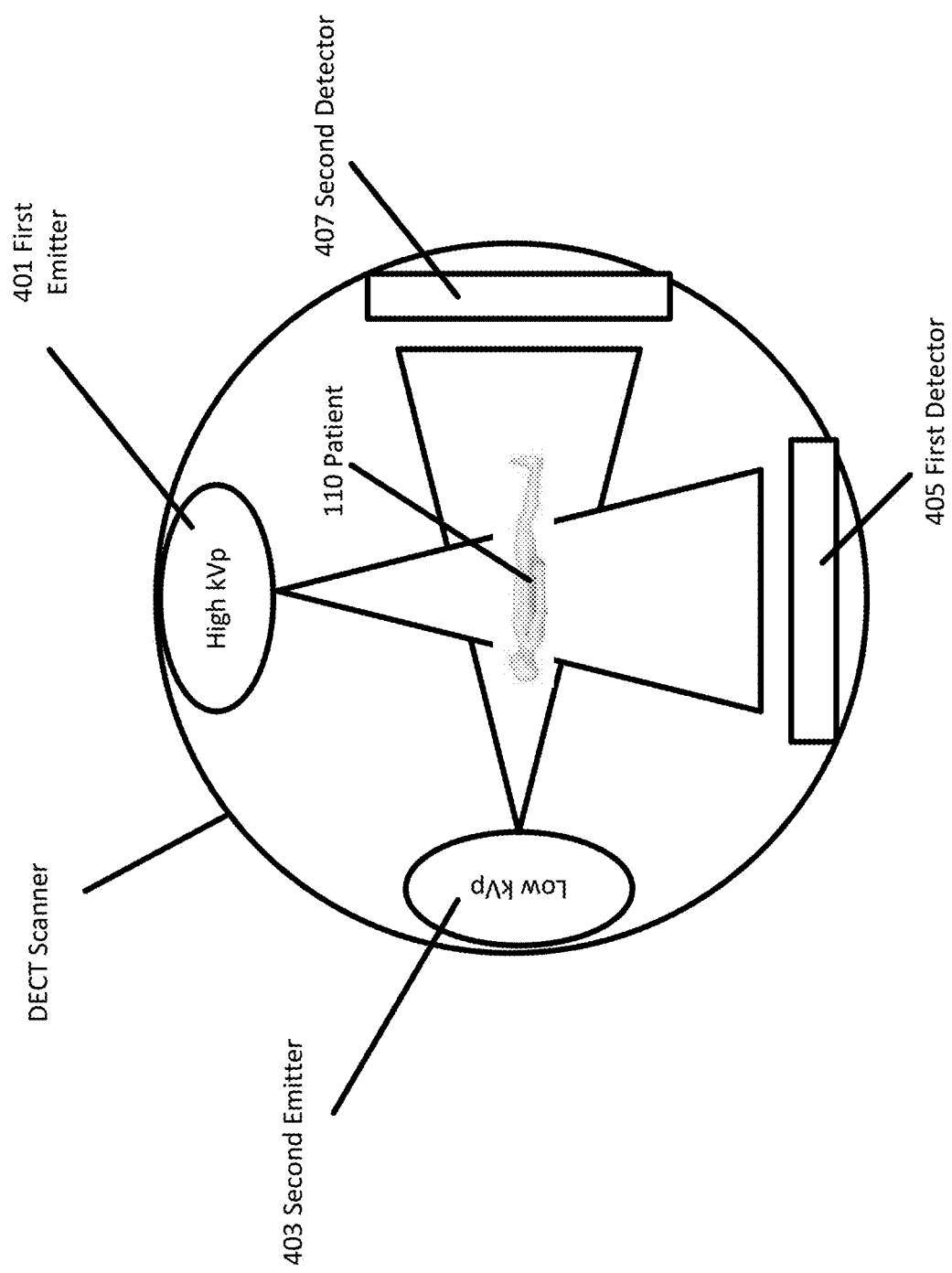
FIG. 4 depicts an example dual energy CT system.

FIG. 4 depicts an example DECT scanner. The DECT scanner includes a first emitter 401, a second emitter 403, a first detector 405, and a second detector 407. The first emitter 401 is configured to generate X-rays with high kVp. The second emitter 403 is configured to generate X-rays with low kVp. The first detector 405 registers information from the first emitter 401. The second detector 407 registers information from the second emitter 403. The first emitter 401, second emitter 403, first detector 405, and the second detector 407 may be configured on a gantry or gantries to rotate around the patient 110.

The DECT scan provides at least two datasets of data of the same object. Because each of the datasets are acquired using different energy levels, the resulting images are different and may be used to differentiate materials, tissues, or fluid. As an example, bone may be easy to identify in a low energy scan while certain tissues may be easy to identify in a high energy scan. If only one scan is used, an operator may have difficulty identify both the bones and tissues of a patient. However, when combining both sets of scan data (that is acquired simultaneously or near simultaneously and are therefore depict the same scene) both the bones and tissues may be identified, leading to a more accurate diagnosis.

In addition to or as an alternative, different settings may be used by the DECT scan to acquire additional data sets. A blended image data set may be created by a combination of the acquired low-energy (80 kVp) and high-energy (140 kVp) data to simulate a 120 kVp dataset. Virtual monochromatic (VMC) or monoenergetic (VME) image data sets may be generated to simulate a scan obtained at a single energy level. The VMC image data sets may be customized to a specific energy level for different clinical applications. Low-energy VMC images may be suggested for studies with high contrast between lesions and adjacent tissues (e.g. CT angiography; 45-55 keV). Intermediate-energy VMC images (60-75 keV) may be used for evaluation of soft tissues due to the balance between adequate contrast and reduced image noise. High-energy VMC images (95-140 keV) may be used to reduce artifacts from metal implants. In an embodiment, multiple VMC images (e.g. ranging from 40 to 140 keV at 10-keV increments) may be reconstructed from the dual-energy datasets by using a projection-based material-decomposition algorithm and mass attenuation of the basis materials. Depending on the imaging system used to acquire the dual-energy data, the approach of basis material decomposition may differ. For dual-energy CT data acquired with a single-source fast-kilovoltage-switching technique, the basis material decomposition is performed in the projection domain. For dual-energy CT data acquired with dual-source CT systems, image domain basis material decomposition is typically used. For VME image data sets, data may be combined from both detectors and additional spectral analysis may be obtained by decomposition of the low and high energy data into photoelectric and Compton data components of attenuation.

The different data sets may be combined or used in combination when input into the machine-learned network 30 described below. For example, different kV level data or monoenergetic images with different keV levels may be acquired or synthesized and used as the input.

In an embodiment, the DECT image data acquired from the DECT scan may be processed to generate one or more additional datasets. A material map may be used to identify different tissues or materials in the datasets. The material map provides values or ranges of values for different materials. DECT image data from the DECT scan is compared against the material map to classify the different materials in the scan. The material map may identify each of the materials in the DECT image data or a subset of materials. Different material maps may be used for different scans, machines, energy levels, and/or settings. Using the material map, each pixel or voxel may be labeled as a certain material, for example, bone or tissue. Vessels and other boundaries may be identified using the material map. Landmarks may be identified in the material map.

In an embodiment, the material map is used with a segmentation process to assign material types to each pixel/voxel in the DECT image data. Any method for segmentation may be used. For example, segmentation may be thresholding-based, region-based, shape-based, model based, neighboring based, and/or machine learning-based among other segmentation techniques. Thresholding-based methods segment the DECT image data by creating binary partitions based on image attenuation values, as determined by the relative attenuation of structures in the DECT image data. Region-based segmentation compares one pixel in a CT image to neighboring pixels, and if a predefined region criterion (e.g. homogeneity) is met, then the pixel is assigned to the same class as one or more of its neighbors. Shape-based techniques use either an atlas-based approach or a model-based approach to find a boundary of an organ or internal structure. Model-based methods use prior shape information, similar to atlas-based approaches; however, to better accommodate the shape variabilities, the model-based approaches fit either statistical shape or appearance models of organs or other bodily structures to the image by using an optimization procedure. Neighboring anatomy-guided methods use the spatial context of neighboring anatomic. In machine learning-based methods, boundaries and materials may be predicted on the basis of the features extracted from the DECT image data.

In an embodiment, an additional dataset is generated that includes a volume with any bone material removed. Bone material may be identified from the segmented data and/or using the material map. Bone material may be masked (e.g. removed) or made transparent.

In an embodiment, an additional dataset is generated that includes vessel tracing. Vessels may be identified from the segmented data and/or by using the material map. Vessels may be highlighted or enhanced. Alternatively, the vessels may be masked or made transparent.

At A120, a bleeding areas are predicted using the DECT image data input into a machine-learned network 30 trained to identify and classify one or more bleeding areas when input DECT image data. In an example, DECT image data from a DECT scan of a patient is input into the machine-learned network 30. The DECT image data may include datasets from the high and low portions of the DECT scan and/or any processed data (e.g. DECT image data that includes bone material removed or vessel tracing). The machine-learned network 30 outputs a map that identifies one or more regions of the patient (and the extent thereof) that depict bleeding.

The machine-learned network 30 is trained to identify bleeding regions or areas using training data that includes already identified traumatic bleeding areas. The training data may be acquired over time by using multiple DECT scans (e.g., samples) of patients and classifying certain regions as bleeding areas (i.e., ground truth). The classifying may be done manually or automatically. The training process includes inputting training data into the machine network, receiving an output, evaluating the output (for example against the already identified bleeding areas), and adjusting the machine network based on the evaluation. The training process may involve hundreds or thousands of iterations. The training process ends when the machine network is capable of identifying the previously identified bleeding areas. The machine-learned network may be updated with new training data or may be manually adjusted to provide more accurate assessments.

In an embodiment, the training may be focused on small patches of the DECT image data so that no spatial relationship is enforced. The machine-learned network 30 may thereby be trained to identify bleeding in any region of the body. One method is to split the input DECT image data into segments or patches. Each segment or patch is then input into the machine-learned network 30 which outputs estimated areas that include bleeding. The patches or segments may be reconstructed into a full body volume or image along with the classification. The training of the machine network may thus disregard any spatial relationships and may be focused on detecting bleeding regardless of the region. The patches or segments may be limited to only include regions of interest or may represent the entirety of the volume acquired by the DECT scan.

In an embodiment, pre-segmented bone and vessel regions may be masked out from the input data by the image processor 25 for training and/or for application. The material map may be used to mask out the bone or vessel regions. Other techniques may be used to preprocess the data as described above in act A110. The masked out regions may include the full body of the patient or only regions of interest.

The machine-learned network 30 is defined as a plurality of sequential feature units or layers. Sequential is used to indicate the general flow of output feature values from one layer to input to a next layer. The information from the next layer is fed to a next layer, and so on until the final output. Skip connections may be used, such as a layer outputting to the sequentially next layer as well as other layers. The layers may only feed forward or may be bi-directional, including some feedback to a previous layer. The nodes of each layer or unit may connect with all or only a sub-set of nodes of a previous and/or subsequent layer or unit.

Rather than pre-programming the features and trying to relate the features to attributes, the deep architecture of the machine-learned network 30 is configured to learn the features at different levels of abstraction based on an input DECT image data with or without pre-processing. The features are learned to reconstruct lower level features (i.e., features at a more abstract or compressed level). For example, features for reconstructing an image are learned. For a next unit, features for reconstructing the features of the previous unit are learned, providing more abstraction. Each node of the unit represents a feature. Different units are provided for learning different features.

Various units or layers may be used, such as convolutional, pooling (e.g., max-pooling), deconvolutional, fully connected, or other types of layers. Within a unit or layer, any number of nodes is provided. For example, 100 nodes are provided. Later or subsequent units may have more, fewer, or the same number of nodes. In general, for convolution, subsequent units have more abstraction. For example, the first unit provides features from the image, such as one node or feature being a line found in the image. The next unit combines lines, so that one of the nodes is a corner. The next unit may combine features (e.g., the corner and length of lines) from a previous unit so that the node provides a shape indication. For transposed-convolution to reconstruct, the level of abstraction reverses. Each unit or layer reduces the level of abstraction or compression. A final layer may classify each pixel or region, for example as depicting a bleeding region or not.

In one embodiment, the arrangement of the machine-learned network 30 is a neural network for deep learning. Other network arrangements may be used, such as a support vector machine, a Siamese network, a generative adversarial network, or other deep architectures. A Siamese network includes two identical networks, each taking one of two input images. The last layers of the two networks are then fed to a contrastive loss function, that is used to calculate the similarity between the two images. The networks learn to differentiate between the two inputs by learning the similarity between them. Other deep architectures include convolutional neural network (CNN) or deep belief nets (DBN). CNN learns feed-forward mapping functions while DBN learns a generative model of data. In addition, CNN uses shared weights for all local regions while DBN is a fully connected network (e.g., including different weights for all regions of an image). The training of CNN is entirely discriminative through back propagation. DBN, on the other hand, employs the layer-wise unsupervised training (e.g., pre-training) followed by the discriminative refinement with back-propagation if necessary. In an embodiment, the arrangement of the machine-learned network 30 is a fully convolutional network (FCN). Alternative network arrangements may be used, for example, a 3D Very Deep Convolutional Networks (3D-VGGNet). VGGNet stacks many layer blocks containing narrow convolutional layers followed by max pooling layers. A 3D Deep Residual Networks (3D-ResNet) architecture may be used. A Resnet uses residual blocks and skip connections to learn residual mapping. Other network architectures may be used, for example, deep reinforcement learning, generative adversarial networks, image-to-image, or U-Net, may also be used among other network architectures. Alternatively, other machine learning implementations may be used that are based on support vector machines, Bayesian classifiers, k-means clustering, decision trees, or inductive programming.

The output of the machine-learned network 30 is a classification of one or more areas as bleeding. Individual pixels or voxels may be classified, or groups of pixels or voxels may be classified. The pixels and voxels may define a probability map that stores values that relate to the predicted bleeding areas using the location of the pixels and voxels. The values may be as simple as a 1 for bleeding predicted and 0 for no bleeding predicted or may be granular and based on a scale. In addition to the classification, the machine-learned network 30 may output a confidence score or probability value that indicates the level of confidence the network includes in the classification.

At A130, a visualization of the bleeding map is generated. The visualization may be generated by the image processor 25 or may be output directly from the machine-learned network 30. The visualization may represent the whole body of the patient or only certain regions. The image processor 25 may process the visualization to include additional data or information relating to the scan, the patient, bleeding, or other information. The visualization may highlight (e.g., graphic or coloring) or visually indicate areas that are classified as bleeding. Areas that are predicted to be bleeding may be rendered with a high level of brightness or with a different color. The visualization may exclude or mask out certain tissues or bone structures. Vessels may be highlighted. In an example, the detected bones and vessels may be removed or set with high transparency to highlight the bleeding area.

At A140, the visualization is displayed by the display 35. The visualization may be provided in real time to an operator and/or may be stored for later use. In an embodiment, the visualization may be used for diagnosis by an operator. A patient may be scanned, and the visualization presented to an operator. The visualization provides an enhanced depiction of the patient and the predicted traumatic bleeding areas. The visualization may be annotated with other data relating to the bleeding area or the patient.

In an embodiment, the visualization is used to provide an overall assessment of traumatic severity and risk. A severity protocol may be generated based on the anatomical spatial relationship, fulfilled by whole body landmark detection using deep reinforcement learning, and generate a severity map for the traumatic bleeding probability map. The diameter, volume, and/or any other metrics of the predicted bleeding areas may be measured. A grade of the bleeding areas may be calculated by combining the size and severity measurement. The findings from the images may be combined with the historical clinical reports to formulate a deep learning-based prediction model to estimate the overall risk to the patient.

Figure 5:
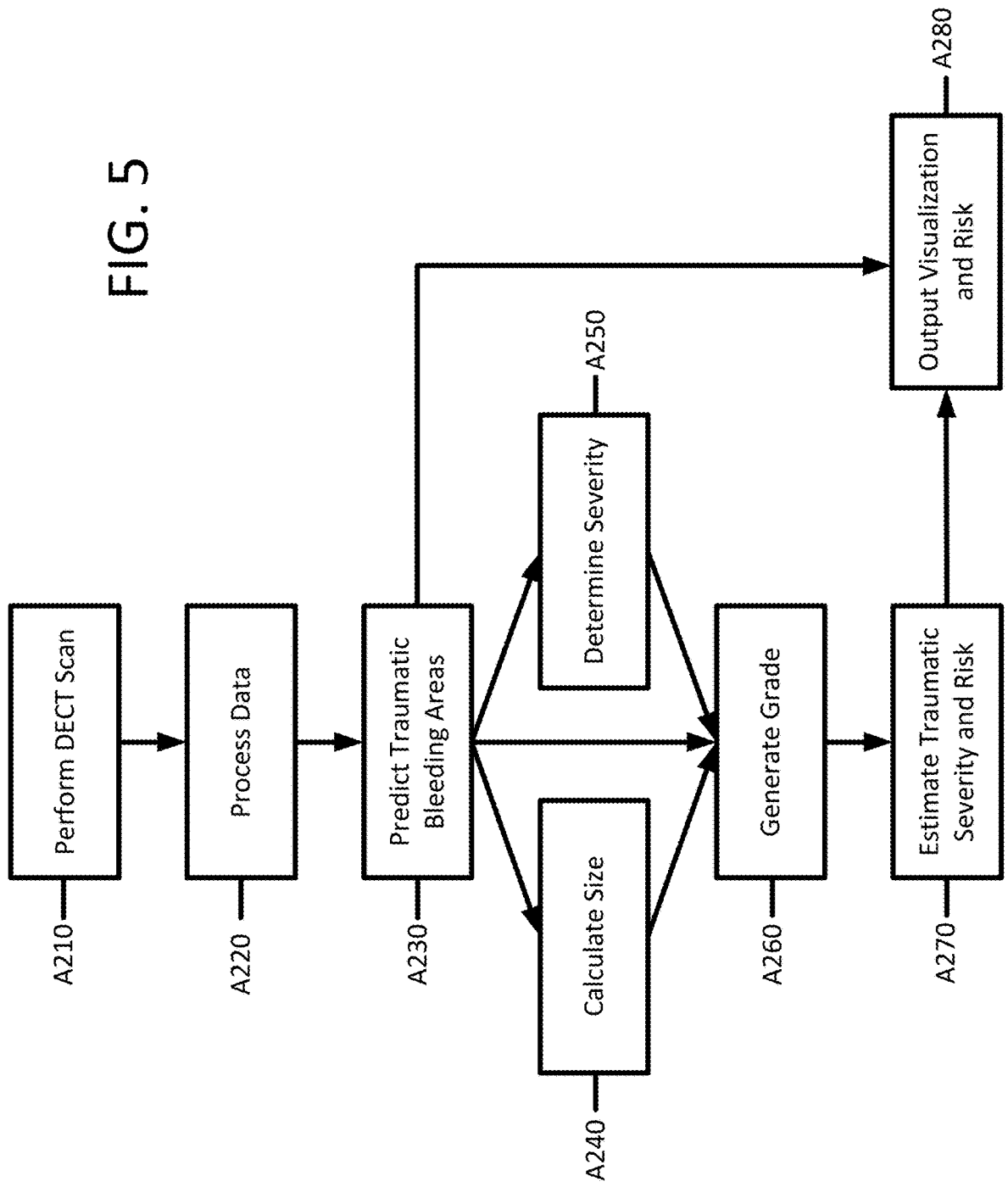
FIG. 5 depicts a method for automated detection and quantification for traumatic bleeding according to an embodiment.

FIG. 5 depicts one embodiment of a method for automatically assessing traumatic bleeding. The acts are performed by the system of FIG. 2, FIG. 4, FIG. 6, other systems, a workstation, a computer, and/or a server. The acts are performed in the order shown (e.g., top to bottom) or other orders. Certain acts may be excluded. For example, the DECT image data may not be processed (act A220) by the image processor 25.

At act A210, DECT image data is acquired using a DECT scan of a patient. In DECT two sets of data are obtained of the same slice, one at lower energy, for example at 80 or 100 kV, the other at higher energy, such as 140 kV. X-rays of different energies may be generated from two emitters. The emitters may be angled 90 degrees from each other. X-rays may also come from a single source that switches between two different energies. Two detectors are used to detect the X-rays. Alternatively, a detector may register data specific to different energies coming from a multi-energy x-ray beam. The data from the DECT may be processed into image data or may be provided as raw data (e.g., scalar values from computed tomography). The DECT image data may be acquired from a PACS, for example, if the scan had previously been performed and the DECT image data stored for later use.

At act A220, the DECT image data is processed by the image processor 25 to remove bone material and trace vessel boundaries. The DECT image data may be 2D or 3D. The DECT image data may be color or grayscale. The DECT image data includes values for pixels (2D) or voxels (3D) derived from the DECT scan. A material map may be used to identify materials that the values represent in the DECT image data. For example, one value (or range of values) may represent bone while another may represent a specific type of tissue. The DECT image data may be segmented to identify boundaries of structures (organs, bone, vessels, etc.). Bone material may then be removed (masked) or rendered transparent. Vessel boundaries may be identified and enhanced (or diminished). The DECT image data for both sets of data (high/low KV) may be processed individually or may be combined and processed together.

At act A230, one or more bleeding areas is predicted using a first machine-learned network 30 trained to identify and classify bleeding areas. The machine-learned network 30 outputs a probability map that predicts one or more regions of the patient (and the extent thereof) that include internal bleeding. The machine-learned network 30 is trained to identify bleeding regions or areas using training data that includes already identified traumatic bleeding areas. The training data may be acquired over time by using multiple DECT scans of patients and classifying certain regions as bleeding areas. The classifying may be done manually or automatically. The training process includes inputting training data into the machine network, receiving an output, evaluating the output (for example against the already identified bleeding areas), and adjusting the machine network based on the evaluation. The training process may involve hundreds or thousands of iterations. The training process ends when the machine network is capable of identifying the previously identified bleeding areas. The machine-learned network may be updated with new training data or may be manually adjusted to provide more accurate assessments.

Different machine-learned network structures and training methods may be used. For example, the machine-learned network architecture may include convolutional neural networks, deep belief networks, deep residual learning, deep reinforcement learning, recurrent neural networks, Siamese networks, generative adversarial networks, or autoencoders among other network architectures. Alternatively, other machine learning implementations may be used that are based on support vector machines, Bayesian classifiers, k-means clustering, decision trees, or inductive programming.

At act A240, a size is calculated for the one or more bleeding areas by an assessor 40. The output of the first machine-learned network 30 includes a classification of the pixels or voxels in the DECT image data. The size, e.g. extent of the bleeding regions is calculated using the classification. The diameter, volume, and/or any other metrics of the bleeding region may be measured from the DECT image data.

At act A250, a severity rating is calculated for the one or more bleeding areas by the assessor 40. The output of the first machine-learned network 30 includes an identification of the bleeding areas. For each bleeding areas, the location of the bleeding areas is identified using landmark detection. The locations are input into a model that identifies the severity of the locations. In a simple example, an area at an extremity may be less severe than an area that is, for example, close to an internal organ. Each predicted bleeding area may be rated individually or together as a group. In addition, the severity rating may be calculated as a function of blood loss. Blood loss may be quantified to predict the risk of a patient undergoing hypovolemic shock. Features such as free blood or hematoma may be used to quantify the already occurred blood loss, features such as contrast blush/ extravasation or lacerations may be used to quantify the ongoing blood loss.

At act A260, a grade is determined by the assessor 40 for the one of more bleeding areas as a function of the size and severity ratings of the one or more bleeding areas. The grade may be determined using a model that is built using prior data, for example clinical reports of previous patients that had traumatic bleeding. Machine learning may be used to generate the model. Alternatively, the grade is determined using a weighted or other function.

At act A270, a risk value is estimated by the assessor 40 for the patient using a second machine-learned network trained to estimate an overall risk. Historical clinical reports of patients may be used as training data for the second machine-learned network. Historical data for traumatic bleeding patients including a size and severity may be input into a machine network. The machine network learns to predict the result given the input data. Other inputs may be used, for example, patient data (size, age, sex, etc.), injury data (e.g., cause of injury, time since injury . . . ), medical procedure data, etc. Different machine-learned network structures and training methods may be used. For example, the second machine-learned network architecture may include convolutional neural networks, deep belief networks, deep residual learning, deep reinforcement learning, recurrent neural networks, Siamese networks, generative adversarial networks, or autoencoders among other network architectures. Alternatively, other machine learning implementations may be used that are based on support vector machines, Bayesian classifiers, k-means clustering, decision trees, or inductive programming. Once trained, the second machine-learned network is configured to output a predicted result given real time patient data derived from the DECT image data and the acts of A220-A260. The predicted result may include a medical diagnosis of the trauma injury and what an operator may expect to occur going forward with the patient. For example, bleeding in one area may result in organ failure if not treated. The predicted result may provide a risk value for the patient to an operator. The predicted result may provide one or more useful procedures to be performed for the patient. At act A280, the risk value and DECT image data (or processed DECT image data) may be presented to an operator using a display 35.

Figure 6:
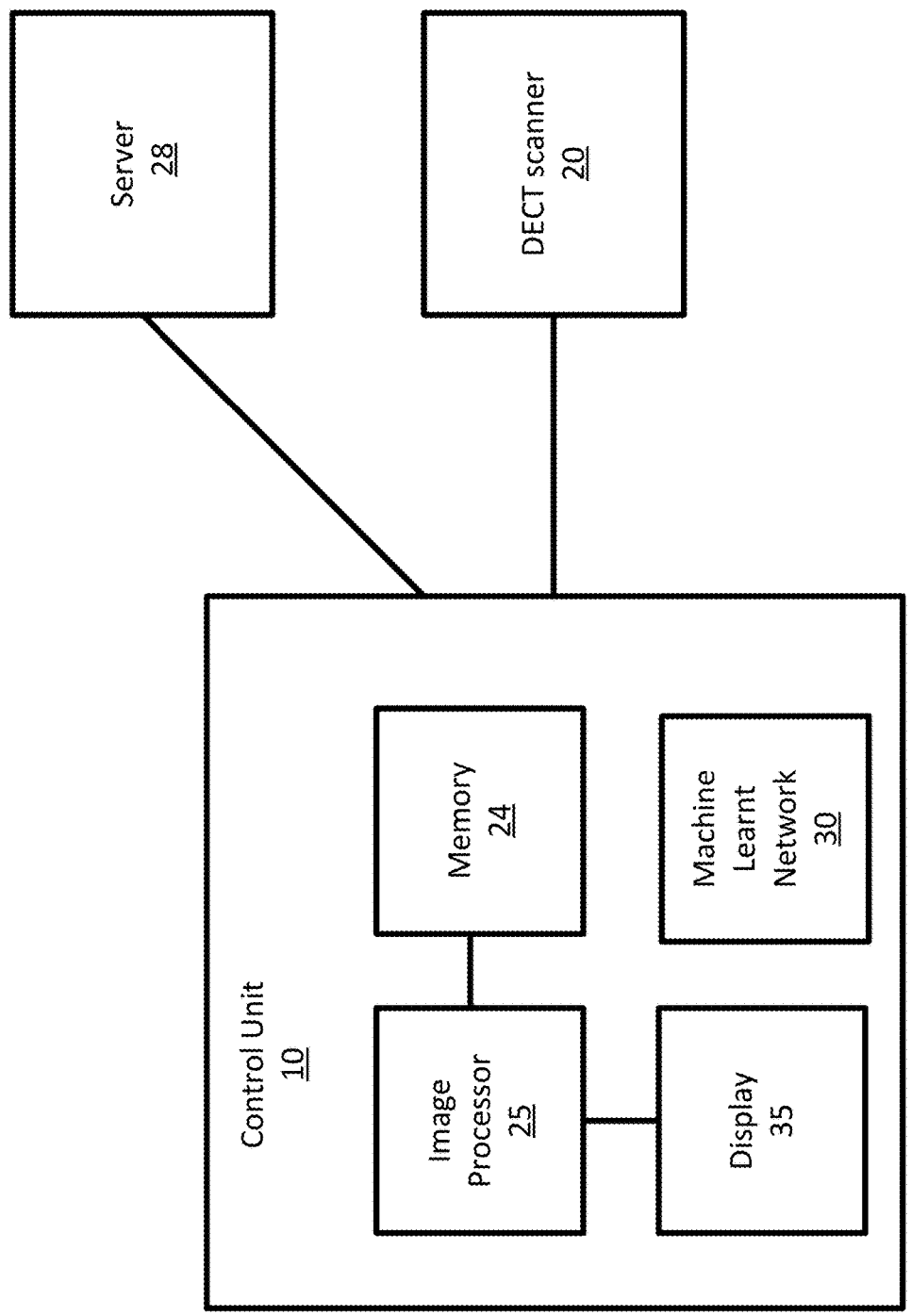
FIG. 6 depicts a system for automated detection and quantification for traumatic bleeding according to another embodiment.

FIG. 6 depicts an embodiment of a system for automatically assessing traumatic bleeding. The system includes a control unit 10, an imaging system 20 (here depicted as a DECT scanner 20), and a server 28. The control unit 10 includes an image processor 25, a memory 24, a display 35, and at least one machine-learned network 30. Additional, different, or fewer components may be provided. For example, network connections or interfaces may be provided, such as for networking with a medical imaging network or data archival system. In another example, a user interface is provided as part of the display 35 or DECT scanner 20. In yet other embodiments, the server 28 or DECT scanner 20 are not provided.

The image processor 25, memory 24, and display 35, machine-learned network 30 are part of the control unit 10. Alternatively, the image processor 25, memory 24, and machine-learned network 30 are part of an archival and/or image processing system, such as associated with a medical records database workstation or server, separate from the DECT scanner 20. In other embodiments, the image processor 25, machine-learned network 30, and memory 24 are a personal computer, such as desktop or laptop, a workstation, a server 28, a network, or combinations thereof. The image processor 25, display 35, machine-learned network 30, and memory 24 may be provided without other components for acquiring data by scanning a patient.

The control unit 10, image processor 25, memory 24, display 35, at least one machine-learned network 30, and DECT scanner 20 are provided at a same location. The location may be a same room, same building, or same facility. The devices are local relative to each other and are remote to the server 28. The server 28 is spaced apart by a network by being in a different facility or by being in a different city, county, state, or country. The server 28 may be remote from the location of the DECT scanner 20.

The DECT scanner 20 is a medical diagnostic imaging system. The DECT scanner 20 is a DECT system. The DECT scanner 20 may include a transmitter and includes a detector for scanning or receiving data representative of the interior of the patient. The DECT scanner 20 is configured to acquire image slices (2D) or an image volume (3D). The DECT scanner 20 may acquire a plurality of image volumes over time that may be used to generate a video.

Two X-ray sources connect to a gantry. Two detectors are also connected with the gantry opposite the X-ray sources. The patient is positioned between the sources and detectors. The sources and detectors are on opposite sides of the patient and rotate and/or translate about the patient. The detected X-ray energy passing through the patient is converted, reconstructed, or transformed into data representing different spatial locations within the patient.

The memory 24 may be a graphics processing memory, a video random access memory, a random-access memory, system memory, cache memory, hard drive, optical media, magnetic media, flash drive, buffer, database, combinations thereof, or other now known or later developed memory device for storing data or video information. The memory 24 is part of the DECT scanner 20, part of a computer associated with the image processor 25, part of a database, part of another system, a picture archival memory, or a standalone device.

The memory 24 stores medical imaging data, graphical or display setting, and/or images. The memory 24 may store data during processing for application and/or may store training data for the machine-learnt network 30. The memory 24 may store data relating to a biomechanical model generated from data acquired from the CT DECT scanner 20.

The memory 24 or other memory is alternatively or additionally a non-transitory computer readable storage medium storing data representing instructions executable by the programmed image processor 25 for automated detection and quantification for traumatic bleeding. The instructions for implementing the processes, methods and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code, and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The machine-learned network 30 may be configured in software or hardware. The machine-learned network 30 may be part of the image processor 25 and/or may be stored in the memory 24. The machine-learned network 30 may be trained on data stored in the memory 24 and/or acquired by the DECT scanner 20. The machine-learned network 30 may be configured to input DECT image data acquired by the DECT scan 20 or stored in memory 24. The machine-learned network 30 may be configured to identify bleeding areas using deep learning and output a bleeding probability map or classification. The deep learning mechanism includes training data, a learning-based evaluation algorithm, and a prediction model. The deep learning mechanism may be based on one of the following architectures: convolutional neural networks, deep belief networks, deep residual learning, deep reinforcement learning, recurrent neural networks, Siamese networks, generative adversarial networks, or autoencoders. Alternatively, other machine learning implementations may be used that are based on support vector machines, Bayesian classifiers, k-means clustering, decision trees, or inductive programming.

Additional machine-learned networks may be trained and stored. The additional machine-learned networks may be part of the image processor 25 and/or may be stored in the memory 24. The additional machine-learned networks may be configured to model risk assessment or a severity of a bleeding area. The additional machine-learned networks may be training using historical clinical reports and previously performed image scans.

The image processor 25 is a general processor, central processing unit, control processor, graphics processing unit, digital signal processor, three-dimensional rendering processor, image processor, application specific integrated circuit, field programmable gate array, digital circuit, analog circuit, combinations thereof, or other now known or later developed device for processing and assessing image data. The image processor 25 is a single device or multiple devices operating in serial, parallel, or separately. The image processor 25 may be a main processor of a computer, such as a laptop or desktop computer, or may be a processor for handling some tasks in a larger system, such as in the DECT scanner 20 or the server 28. The image processor 25 is configured by instructions, design, hardware, and/or software to perform the acts discussed herein.

The image processor 25 and/or server 28 are configured to perform the acts discussed above for performing automated detection and quantification for traumatic bleeding on Dual Energy CT using deep learning techniques. The image processor 25 is configured to provide bone removal solution that may be improved using a material map. The image processor 25 is configured to provide vessel tracing solution that may be improved with the material map. The image processor 25 may be configured to quantify blood loss to predict the risk of a patient undergoing hypovolemic shock. The image processor 25 may be configured to generate a visualization of the bleeding areas with the detected bones and vessels removed or set with high transparency to highlight the bleeding area. The image processor 25 may be configured to measure the diameter, volume, and/or any other metrics of the predicted bleeding areas. The image processor 25 may be configured to pre-build a severity protocol based on an anatomical spatial relationship, fulfilled by whole body landmark detection using deep reinforcement learning, and generate a severity map. The image processor 25 may be configured to combine the size and severity measurement to calculate an overall grade to each predicted bleeding areas. The image processor 25 may be configured to combine the findings from the images with the historical clinical reports to formulate a deep learning based prediction model to estimate the overall risk.

The image processor 25 and/or server 28 are configured to provide an image to the display 35 or to the memory 24. The display 35 is a monitor, LCD, projector, plasma display, CRT, printer, or other now known or later developed devise for outputting visual information. The display 35 receives images, graphics, text, quantities, or other information from the image processor 25, memory 24, DECT scanner 20, and/or server 28. The display 35 is configured to provide image volumes to an operator.

The control unit 10 may also include a user interface (not shown) that is configured to receive one or more selections from a user. The user interface may include an input device such as one or more buttons, a keypad, a keyboard, a mouse, a stylus pen, a trackball, a rocker switch, a touch pad, a voice recognition circuit, or other device or component for inputting data. The user interface and the display 35 may be combined as a touch screen that may be capacitive or resistive.

The server 28 connects to the DECT scanner 20 via a network. The network is a local area, wide area, enterprise, another network, or combinations thereof. In one embodiment, the network is, at least in part, the Internet. Using TCP/IP communications, the network provides for communication between the image processor 25 and the server 28. Any format for communications may be used. In other embodiments, dedicated or direct communication is used.

The server 28 is a processor or group of processors. More than one server 28 may be provided. The server 28 is configured by hardware and/or software. The server 28 may include one or more image processors 25. The one or more image processors 25 may operate serially or in parallel to process and render DECT image data received from the DECT scanner 20.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A method for predicting bleeding areas in a patient, the method comprising:
    acquiring dual energy image data comprising two or more datasets of computed tomography (CT) data using a dual energy computed tomography full body scan of the patient;
    predicting one or more bleeding areas on a bleeding area map using a neural network trained to identify and classify bleeding areas when input the two or more datasets of CT data acquired using two different energy levels;
    generating a visualization of the one or more bleeding areas; and
    displaying the visualization.

2. The method of claim 1, wherein the two or more datasets of CT data comprises at least
    high kilovolt (kV) CT image data and low kV CT image data.

3. The method of claim 1, further comprising:
    synthesizing virtual monochromatic image data from the dual energy image data;
    wherein the synthesized virtual monochromatic image data is used for detecting the bleeding areas.

4. The method of claim 1, further comprising:
    wherein the dual energy image data comprises monoenergetic image data with different Kilo Electron Volt (keV) levels.

5. The method of claim 1, further comprising:
    processing the dual energy image data to remove bone material and trace vessels.

6. The method of claim 5, wherein processing comprises:
    identifying material types in the dual energy image data using a material map;
    segmenting the dual energy image data using the material types;
    masking out bone material using the segmented dual energy image data; and
    tracing vessels using the segmented dual energy image data.

7. The method of claim 1, wherein the neural network is a convolutional neural network.

8. The method of claim 7, wherein the neural network is trained using manually annotated full body images of bleeding patients.

9. The method of claim 1, further comprising:
    identifying one or more regions of interest in the dual energy image data;
    inputting image data for the one or more regions of interesting into the neural network in place of the dual energy image data.

10. The method of claim 1, further comprising:
    quantifying a severity of the one or more bleeding areas;
    wherein the visualization is generated with an indication of the quantification for the one or more bleeding areas.

11. A system for automatically assessing traumatic bleeding, the system comprising:
    a dual energy computer tomography (CT) scanner configured to acquire high kilovolt (kV) CT image data and low kV CT image data of a patient;
    an image processor configured to input the high kV CT image data and low kV CT image data into a machine-learned network trained to predict bleeding areas given image data; the image processor further configured to generate a visualization of the bleeding areas predicted by the machine-learned network; and
    a display configured to display the visualization.

12. The system of claim 11, wherein the dual energy computer tomography scanner is configured to perform a full body scan of the patient.

13. The system of claim 11, further comprising:
    an assessment module configured to estimate a risk value for the patient using a second machine-learned network trained to formulate an overall risk given one or more predicted bleeding areas.

14. The system of claim 13, wherein the assessment module is further configured to estimate the risk value by calculating a size and severity rating for the one or more predicted bleeding areas.

* * * * *